United States Patent [19]

VandenBerg

[11] Patent Number: 5,850,006
[45] Date of Patent: *Dec. 15, 1998

[54] CUT FLOWERS AND PROPAGATING MATERIAL OF THE CHRYSANTHEMUM PLANT NAMED MODA

[75] Inventor: Cornelis P. VandenBerg, Salinas, Calif.

[73] Assignee: Yoder Brothers, Inc., Alva, Fla.

[*] Notice: The portion of the term of this patent subsequent to Jun. 27, 2006, has been disclaimed.

[21] Appl. No.: 229,117

[22] Filed: Aug. 5, 1988

Related U.S. Application Data

[62] Division of Ser. No. 173,086, Mar. 25, 1988, Pat. No. Plant 6,886.

[51] Int. Cl.⁶ .............................. A01H 5/00; A01H 1/00
[52] U.S. Cl. ................................. 800/200; 800/DIG. 12; 47/58; 47/DIG. 1; Plt./78; Plt./74.1
[58] Field of Search .................. Plt./78, 74.1; 800/1, 800/200, DIG. 12; 47/58, DIG. 1

[56] References Cited

U.S. PATENT DOCUMENTS

| | | | |
|---|---|---|---|
| P.P. 5,713 | 4/1986 | Duffett | Plt./78 |
| P.P. 6,886 | 6/1989 | VandenBerg | Plt./78 |
| P.P. 6,904 | 7/1989 | VandenBerg | Plt./78 |
| P.P. 7,992 | 9/1992 | Hesse | Plt./78 |

OTHER PUBLICATIONS

Searle et al (1968) Chrysanthemum The Year Round, London, Blanford Press, pp. 19–29.

Whealy Cultivar Selection Con Minimize Chrysanthemum Heat Delay *On Grower Stalk*.

*Primary Examiner*—Gary Benzion
*Attorney, Agent, or Firm*—Foley & Lardner

[57] ABSTRACT

A Chrysanthemum plant named Moda particularly characterized by its flat capitulum form; pompon capitulum type; yellow ray floret color; diameter across face of capitulum of up to 4 cm at maturity; uniform eight week photoperiodic flowering response to short days; peduncle length ranging from 5 to 15 cm on open, terminal sprays; medium plant height when grown as a single stem spray cut mum; and excellent tolerance to low temperatures for bud initiation and flower development.

2 Claims, 1 Drawing Sheet
(1 of 1 Drawing Sheet Filed in Color)

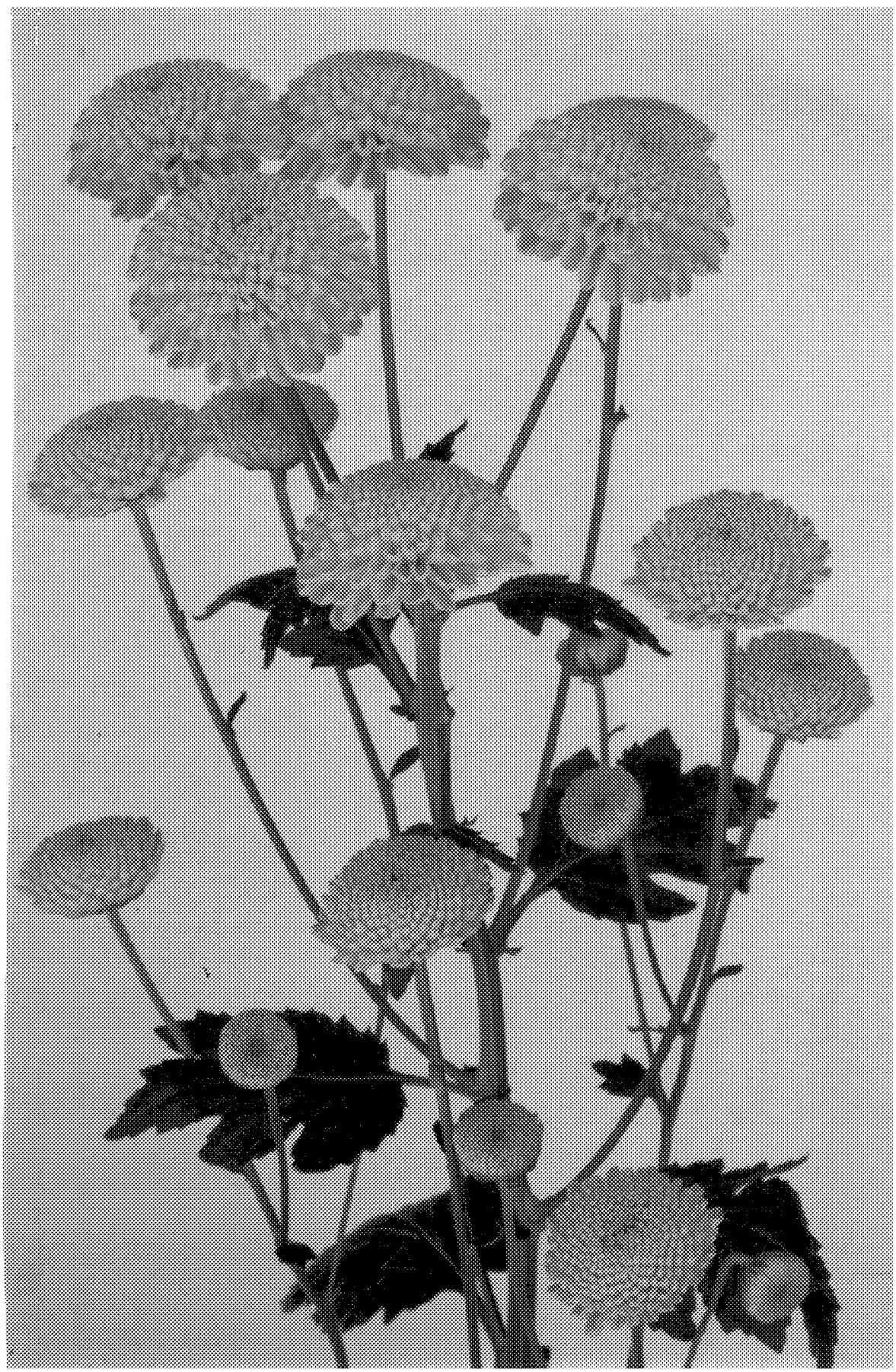

CUT FLOWERS AND PROPAGATING MATERIAL OF THE CHRYSANTHEMUM PLANT NAMED MODA

This is a division of application Ser. No. 173,086, filed Mar. 25, 1988, U.S. Plant Pat. No. 6,886.

The present invention comprises a new and distinct cultivar of Chrysanthemum, botanically known as *Dendranthema grandiflora*, and referred to by the cultivar name Moda.

Moda, identified as 84Y45007, was originated from a cross made by Cornelis P. VandenBerg in a controlled breeding program in Salinas, Calif. in 1983.

The female parent of Moda was the cultivar identified as Statesman, an unpatented cultivar. The male parent of Moda was an unnamed seedling, identified as 81765003.

Moda was discovered and selected as one flowering plant within the progeny of the stated cross by Cornelis P. VandenBerg in July of 1984 in a controlled environment in Salinas, Calif.

The first act of asexual reproduction of Moda was accomplished when propagating material in the form of vegetative cuttings were taken from the initial selection in September 1984 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Moda are firmly fixed and are retained through successive generations of asexual reproduction.

Moda has not been observed under all possible environmental conditions. The phenotype may vary significantly with variations in environment such as temperature, light intensity, and daylength.

The following observations, measurements and comparisons describe plants grown in Salinas, Calif. under greenhouse conditions which approximate those generally used in commercial greenhouse practice. The low temperature tolerance was determined in repeated flowerings in Bogota, Colombia.

The following traits have been repeatedly observed and are determined to be basic characteristics of Moda, which, in combination, distinguish this cut flower Chrysanthemum as a new and distinct cultivar:

1. Flat capitulum form.
2. Pompon capitulum type.
3. Yellow ray floret color.
4. Diameter across face of capitulum up to 4 cm at maturity.
5. Uniform eight week photoperiodic flowering response to short days.
6. Peduncle length ranging from 5 to 15 cm on open terminal sprays.
7. Medium plant height, requiring two long day weeks prior to short days to attain a flowered plant height of 90 to 100 cm for year-round flowerings.
8. Excellent tolerance to low temperatures for bud initiation and flower development.

The accompanying photographic drawings show typical inflorescence and leaf characteristics of Moda.

BRIEF DESCRIPTION OF THE APPLICATION DRAWINGS

The file of this patent contains at least one drawing executed in color. A copy of this patent with a color drawing will be provided by the Patent and Trademark Office upon request and payment of the necessary fee.

The accompanying photographic drawing shows typical inflorescence and leaf characteristics of Moda, with the colors being as nearly true as possible with illustrations of this type. FIG. 1 comprises a color photograph illustrating in perspective view a plant of Moda grown as a single stem cut spray mum.

Similar traits are ray floret color and capitulum form and type. The spray formation of Moda is always terminal, while the spray formation of Statesman is compound. Moda has a larger diameter of capitulum, a taller plant height, a faster flowering response and a better low temperature tolerance than Statesman. Under adverse conditions Statesman exhibits foliar sensitivity to chemical sprays. Moda's foliage has not shown any sensitivity to sprays used in trials.

In the following description, color references are made to The Royal Horticultural Society Colour Chart. The color values were determined on plant material grown in Salinas, Calif. on Oct. 12, 1987.

CLASSIFICATION:
    Botanical.—*Dendranthema grandiflora*, cv Moda.
    Commercial.—Pompon cut spray mum.

Inflorescence

A. Capitulum:
    Form: Flat.
    Type: Pompon.
    Diameter across face: Up to 4 cm at maturity.

B. Corolla of ray florets:
    Color (general tonality from a distance of three meters).—Yellow.
    Color (upper surface).—14A.
    Color (under surface).—12A.
    Shape.—Straight; convex.

C. Corolla od disc florets:
    Color (mature).—Closest to 5A.
    Color (immature).—Closest to 151B.

D. Reproductive organs:
    Androecium.—Present on disc florets only; very few disc florets, barely visible in the mature flower; scant pollen.
    Gynoecium.—Present on both ray and disc florets.

Plant

A. General apperance:
    Height.—Medium; 90 to 100 cm as a single stem cut mum with 2 long day weeks prior to short days.

B. Foliage:
    Color (upper surface).—147A.
    Color (under surface).—147B.
    Shape.—Lobed and slightly serrated.

CHART A

| COMPARISON OF MODA AND STATESMAN | | |
|---|---|---|
|  | Moda | Statesman |
| Ray floret color | Yellow | Yellow |
| Capitulum form | Flat | Flat |
| and type | Pompon | Pompon |
| Spray formation | Terminal | Compound |
| Diameter across face of capituium | Up to 4 cm | Up to 3 cm |
| Plant height | Medium | Short |

CHART A-continued

COMPARISON OF MODA AND STATESMAN

|  | Moda | Statesman |
|---|---|---|
| Flowering response period | 8 weeks | 9 weeks |
| Low temperature tolerance | Excellent | Good |

COMPARISONS MADE OF PLANTS GROWN AS SINGLE STEM CUT SPRAY MUMS IN SALINAS, CALIFORNIA

I claim:

1. Cut flowers of the chrysanthemum plant named Moda having the combined characteristics of flat capitulum form, pompon capitulum type, capitulum diameter of up to 4 cm at maturity, ray floret color of RHS 14A for upper surface of flower, mature disc floret color of approximately RHS 5A, uniform eight week photoperiodic flower response to short days, excellent tolerance to low temperatures for bud initiation and flower development, and lobed and slightly serrated leaves the upper surfaces of which are RHS 147A in color.

2. Propagating material of the chrysanthemum plant named Moda which has the combined characteristics of flat capitulum form, pompon capitulum type, capitulum diameter of up to 4 cm at maturity, ray floret color of RHS 14A for upper surface of flower, mature disc floret color of approximately RHS 5A, uniform eight week photoperiodic flower response to short days, excellent tolerance to low temperatures for bud initiation and flower development, and lobed and slightly serrated leaves the upper surfaces of which are RHS 147A in color.

* * * * *